United States Patent
Hoitink et al.

(10) Patent No.: US 10,463,425 B2
(45) Date of Patent: Nov. 5, 2019

(54) RF ABLATION WITH ACOUSTIC FEEDBACK

(71) Applicant: Biosense Webster (Israel) Ltd., Yokneam (IL)

(72) Inventors: Ryan A. Hoitink, Glendale, CA (US); John Hardy Ashton, Glendora, CA (US); Jeffrey L. Clark, Castaic, CA (US); Kelvin Chuu, Hermosa Beach, CA (US); Jeffrey Schultz, Chino, CA (US)

(73) Assignee: Biosense Webster (Israel) Ltd., Yokneam (IL)

( * ) Notice: Subject to any disclaimer, the term of this patent is extended or adjusted under 35 U.S.C. 154(b) by 335 days.

(21) Appl. No.: 14/703,542

(22) Filed: May 4, 2015

(65) Prior Publication Data
US 2016/0324569 A1 Nov. 10, 2016

(51) Int. Cl.
*A61B 18/14* (2006.01)
*A61B 18/12* (2006.01)
*A61B 18/00* (2006.01)

(52) U.S. Cl.
CPC ...... *A61B 18/1492* (2013.01); *A61B 18/1206* (2013.01); *A61B 2018/00029* (2013.01); *A61B 2018/00577* (2013.01); *A61B 2018/00636* (2013.01); *A61B 2018/00702* (2013.01); *A61B 2018/00744* (2013.01); *A61B 2018/00791* (2013.01); *A61B 2018/00875* (2013.01); *A61B 2018/00898* (2013.01); *A61B 2218/002* (2013.01)

(58) Field of Classification Search
CPC ............ A61B 18/1206; A61B 18/1492; A61B 2018/00029; A61B 2018/00577; A61B 2018/00636; A61B 2018/00702; A61B 2018/00744; A61B 2018/00791; A61B 2018/00875; A61B 2018/00898; A61B 2218/002
See application file for complete search history.

(56) References Cited

U.S. PATENT DOCUMENTS

| | | | |
|---|---|---|---|
| 5,391,199 A | | 2/1995 | Ben-Haim |
| 5,733,281 A | * | 3/1998 | Nardella ............ A61B 18/1206 606/38 |
| 6,239,724 B1 | | 5/2001 | Doron et al. |
| 6,332,089 B1 | | 12/2001 | Acker et al. |
| 6,484,118 B1 | | 11/2002 | Govari |
| 6,618,612 B1 | | 9/2003 | Acker et al. |
| 6,690,963 B2 | | 2/2004 | Ben-Haim et al. |
| 8,147,484 B2 | * | 4/2012 | Lieber ................. A61B 5/0084 600/475 |
| 8,162,933 B2 | * | 4/2012 | Francischelli ..... A61B 18/1442 128/898 |

(Continued)

FOREIGN PATENT DOCUMENTS

WO   96/05768 A1   2/1996

OTHER PUBLICATIONS

European Search Report and Written Opinion for Europe Application No. 16168007.9, dated Jul. 8, 2016.

(Continued)

*Primary Examiner* — Michael F Peffley
(74) *Attorney, Agent, or Firm* — Dergosits & Noah LLP; Todd A. Noah

(57) ABSTRACT

Systems and methods are disclosed for performing an ablation procedure by obtaining a signal from an acoustic sensor used to detect occurrence of a steam pop and adjust the ablation in response to the steam pop detection.

23 Claims, 5 Drawing Sheets

(56) References Cited

U.S. PATENT DOCUMENTS

| | | | |
|---|---|---|---|
| 2002/0058933 A1 | 5/2002 | Christopherson et al. | |
| 2002/0065455 A1 | 5/2002 | Ben-Haim et al. | |
| 2003/0120150 A1 | 6/2003 | Govari | |
| 2003/0204184 A1* | 10/2003 | Ferek-Patric | A61B 18/1492 606/41 |
| 2004/0068178 A1 | 4/2004 | Govari | |
| 2010/0168572 A1 | 7/2010 | Sliwa et al. | |
| 2011/0144524 A1* | 6/2011 | Fish | A61B 18/1492 600/547 |
| 2013/0296850 A1 | 11/2013 | Olson | |
| 2015/0005758 A1* | 1/2015 | Berger | A61B 18/1233 606/34 |
| 2017/0020395 A1* | 1/2017 | Malchano | A61B 1/05 |

OTHER PUBLICATIONS

European Office Action for Europe Application No. 1618007.9, dated Oct. 5, 2017.
William W.B. Chik et al, "Acoustic Signal Emission Monitoring as a Novel Method to Predict Steam Pops During Radiofrequency Ablation: Preliminary Observations", Journal of Cardiovascular Electrophysiology., US, (Apr. 14, 2015), vol. 26, No. 4, doi:10.1111/jce.12598, ISSN 1045-3873, pp. 440-447, XP055282429 [X] 3-9 * Methods Section, Results Section, Clinical Implications Section; p. 441-p. 446.
Visitag et al, (Dec. 31, 2014), URL: https://www.biosensewebster.com/documents/SmartTouchSFSellSheetP46987.pdf?Cache=28/05/2015 00:38:44, (Jul. 8, 2016), XP055286938.

* cited by examiner

RF ABLATION WITH ACOUSTIC FEEDBACK

FIELD OF THE PRESENT DISCLOSURE

This disclosure relates generally to methods and devices for percutaneous medical treatment, and specifically to controlling the delivery of RF energy in response to acoustic feedback.

BACKGROUND

Radiofrequency (RF) electrode catheters have been in common use in medical practice for many years. They are used to stimulate and map electrical activity in the heart and to ablate sites of aberrant electrical activity. Specifically, targeted ablation may be performed for a number of indications. For example, ablation of myocardial tissue is well known as a treatment for cardiac arrhythmias by using a catheter to apply RF energy and create a lesion to break arrhythmogenic current paths in the cardiac tissue. As another example, a renal ablation procedure may involve the insertion of a catheter having an electrode at its distal end into a renal artery in order to complete a circumferential lesion in the artery in order to denervate the artery for the treatment of hypertension. More generally, RF energy may be delivered to a treatment site within a patient's body to ablate tissue and/or to form a lesion.

In such procedures, a reference electrode is typically provided and may be attached to the skin of the patient or by means of a second catheter. RF current is applied between the tip electrode of the ablating catheter and the reference electrode, and current flows through the media that surrounds them, i.e., blood and tissue. The distribution of current from the ablation tip electrode depends on the amount of electrode surface in contact with the tissue as compared to blood, which has a higher conductivity than the tissue. Heating of the tissue occurs due to its electrical resistance. The tissue is heated to a desired degree, such as an amount sufficient to cause cellular destruction in the target tissue resulting in formation of a lesion which is electrically non-conductive. The lesion may be formed in tissue contacting the electrode or in adjacent tissue.

Although such techniques involve the intentional heating of tissue in order to effect a change in the patient's physiology, it is desirable to control the amount of energy delivered to reduce collateral damage to tissue surrounding the treatment area. Notably, during RF ablation, the delivery of energy may be sufficient to vaporize water present at the treatment site, resulting in a phenomenon known as a "steam pop." The rapid increase in volume associated with the transition of water from liquid phase to gas phase transmits force to the surrounding tissue and has the potential to cause adverse results, such as thrombus formation, perforation of tissue and/or tamponade.

To reduce the occurrence of these and other negative consequences of a steam pop, the attending electrophysiologist typically ceases delivery of RF energy to the current treatment site when a steam pop is audible. However, it will be appreciated that this conventional practice does not represent an optimum technique for controlling the delivery of energy during an ablation procedure. For example, steam pops may occur during a procedure that are inaudible for a variety of reasons, such as location of the treatment site or magnitude of the pop. Further, even if a resulting steam pop is audible, there may be a delay in the reaction time of the electrophysiologist, so that RF energy continues to be delivered for a period of time after detection of the pop. Under these or other circumstances, RF energy may continue to be delivered despite the occurrence of steam pops, leading to an increased risk of the noted adverse events.

Accordingly, it would be desirable to provide methods and systems for improving the detection of steam pops during an RF ablation procedure. Similarly, it would be desirable to reduce the amount of time required to cease delivery of RF energy or otherwise adjust the ablation after a steam pop is detected. As will be described in the following materials, this disclosure satisfies these and other needs.

SUMMARY

The present disclosure is directed to a method for the ablation of a portion of tissue of a patient by an operator including inserting an ablation catheter having an electrode into the patient, connecting the catheter to a system controller capable of delivering power to the electrode, delivering power to the electrode to ablate tissue, obtaining a signal from an acoustic sensor, detecting occurrence of a steam pop based at least in part on the acoustic sensor signal and adjusting the ablation in response to the steam pop detection.

In one aspect, adjusting the ablation may include ceasing delivery of power to the electrode.

In one aspect, adjusting the ablation may include attenuating the power delivered to the electrode. The power may be attenuated based at least in part on a characteristic determined from the acoustic sensor signal.

In one aspect, adjusting the ablation may include reducing a contact force of the electrode.

In one aspect, adjusting the ablation may include altering delivery of irrigation fluid.

In one aspect, obtaining the signal from the acoustic sensor may include positioning the acoustic sensor adjacent the patient, positioning the acoustic sensor in contact with the patient and/or positioning the acoustic sensor within the patient. The acoustic sensor may be carried by the ablation catheter.

In one aspect, obtaining the signal from the acoustic sensor may include deploying a plurality of acoustic sensors.

In one aspect, obtaining the signal from the acoustic sensor may include processing the signal to facilitate identification of a steam pop.

In one aspect, the system controller may have an acoustic module configured to receive the acoustic sensor signal such that a steam pop may be identified with the acoustic module based at least in part on the acoustic sensor signal. The acoustic module may also receive information from an additional sensor and the steam pop may be identified based at least in part on the information from the additional sensor. For example, the steam pop may be identified based at least in part on an increase in impedance and/or temperature measured by the additional sensor.

In one aspect, the operator may be alerted when the acoustic module indentifies a steam pop.

In one aspect, an identification criterion employed by the acoustic module may be adjusted.

In one aspect, the delivery of power to the electrode may be automatically adjusted when the acoustic module identifies a steam pop. The delivery of power may be adjusted based at least in part on a measured characteristic of the steam pop. Alternatively, the delivery of power to the electrode may be automatically ceased when the acoustic module identifies a steam pop.

This disclosure is also directed to a catheter having an elongated body, an electrode mounted at a distal end of the elongated body, wherein the electrode is configured to deliver energy to ablate tissue and an acoustic sensor configured to output a signal that may be used to detect an occurrence of a steam pop.

In one aspect, the catheter may have a temperature sensor mounted at the distal end of the elongated body.

Further, this disclosure is directed to an ablation system having an ablation catheter with an electrode configured to be inserted into a patient, a system controller capable of delivering power to the electrode and an acoustic sensor to output a signal that may be used to detect an occurrence of a steam pop.

In one aspect, the system may include an acoustic module to identify a steam pop based at least in part on the acoustic sensor signal.

In one aspect, the system may include an additional sensor, wherein the acoustic module may receive information from the additional sensor and identify the steam pop based at least in part on the information from the additional sensor. The additional sensor may measure impedance and/or temperature.

In one aspect, the system may include an indicator to alert an operator when the acoustic module indentifies a steam pop.

In one aspect, the system may include an ablation module to automatically adjust the delivery of power to the electrode when the acoustic module identifies a steam pop.

BRIEF DESCRIPTION OF THE DRAWINGS

Further features and advantages will become apparent from the following and more particular description of the preferred embodiments of the disclosure, as illustrated in the accompanying drawings, and in which like referenced characters generally refer to the same parts or elements throughout the views, and in which.

DETAILED DESCRIPTION

At the outset, it is to be understood that this disclosure is not limited to particularly exemplified materials, architectures, routines, methods or structures as such may vary. Thus, although a number of such options, similar or equivalent to those described herein, can be used in the practice or embodiments of this disclosure, the preferred materials and methods are described herein.

It is also to be understood that the terminology used herein is for the purpose of describing particular embodiments of this disclosure only and is not intended to be limiting.

The detailed description set forth below in connection with the appended drawings is intended as a description of exemplary embodiments of the present disclosure and is not intended to represent the only exemplary embodiments in which the present disclosure can be practiced. The term "exemplary" used throughout this description means "serving as an example, instance, or illustration," and should not necessarily be construed as preferred or advantageous over other exemplary embodiments. The detailed description includes specific details for the purpose of providing a thorough understanding of the exemplary embodiments of the specification. It will be apparent to those skilled in the art that the exemplary embodiments of the specification may be practiced without these specific details. In some instances, well known structures and devices are shown in block diagram form in order to avoid obscuring the novelty of the exemplary embodiments presented herein.

For purposes of convenience and clarity only, directional terms, such as top, bottom, left, right, up, down, over, above, below, beneath, rear, back, and front, may be used with respect to the accompanying drawings. These and similar directional terms should not be construed to limit the scope of the disclosure in any manner.

Unless defined otherwise, all technical and scientific terms used herein have the same meaning as commonly understood by one having ordinary skill in the art to which the disclosure pertains.

Finally, as used in this specification and the appended claims, the singular forms "a, "an" and "the" include plural referents unless the content clearly dictates otherwise.

Figure 1:
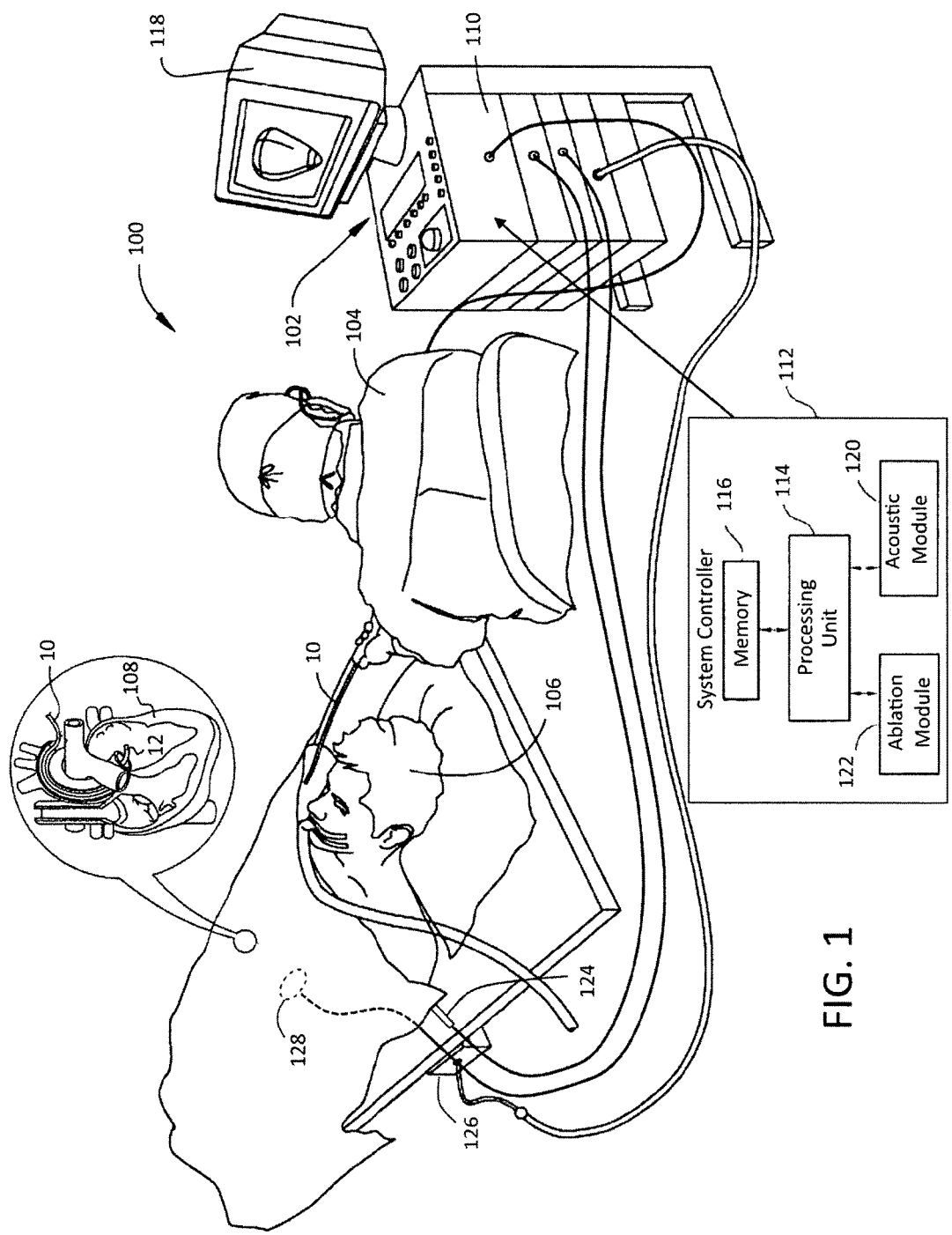
FIG. 1 is a schematic view of an ablation system in accordance with an embodiment of the present invention.

As noted above, a catheter may be used to deliver RF energy to a selected position within a patient in a variety of therapeutic and diagnostic contexts. As illustration only as an example, and without limitation, one suitable procedure according to this disclosure may involve an ablation procedure following techniques known to those of skill in the art. FIG. 1 is a schematic, pictorial illustration of a system 100 for renal and/or cardiac catheterization and ablation, in accordance with an embodiment of the present invention. System 100 may be based, for example, on the CARTO™ mapping systems, produced by Biosense Webster Inc. (Diamond Bar, Calif.) and/or SmartAblate or nMarq RF generators. This system comprises an invasive probe in the form of catheter 10 and a control and/or ablation console 102. An operator 104, such as a cardiologist, electrophysiologist or interventional radiologist, inserts ablation catheter 10 into and through the body of a patient 106, such as through a femoral or radial access approach, so that a distal end of catheter 10, in particular, electrode 12, engages tissue at a desired location or locations, such as a chamber of heart 108 of patient 106. Catheter 10 is typically connected by a suitable connector at its proximal end to console 102. Console 102 comprises a RF generator 110, which supplies high-frequency electrical energy via the catheter for ablating tissue at the locations engaged by electrode 12.

Console 102 may also use magnetic position sensing to determine position coordinates of the distal end of catheter 10 inside the body of the patient 106. For this purpose, a driver circuit in console 102 drives field generators to generate magnetic fields within the body of patient 106. Typically, the field generators comprise coils, which are placed below the patient's torso at known positions external to the patient. These coils generate magnetic fields in a predefined working volume that contains the area of interest. A magnetic field sensor within distal end of catheter 10 generates electrical signals in response to these magnetic fields. A signal processor in console 102 may process these signals in order to determine the position coordinates of the distal end, typically including both location and orientation coordinates. This method of position sensing is implemented in the above-mentioned CARTO system and is described in detail in U.S. Pat. Nos. 5,391,199, 6,690,963, 6,484,118, 6,239,724, 6,618,612 and 6,332,089, in PCT Patent Publication WO 96/05768, and in U.S. Patent Application Publications 2002/0065455 A1, 2003/0120150 A1 and 2004/0068178 A1, whose disclosures are all incorporated herein by reference.

Console 102 may include system controller 112, comprising a processing unit 114 communicating with a memory 116, wherein is stored software for operation of system 100. Controller 112 may be an industry standard personal computer comprising a general purpose computer processing unit. However, in some embodiments, at least some of the functions of the controller are performed using custom designed application specific integrated circuits (ASICs), a field programmable gate array (FPGA) or other similar components. Controller 112 is typically operated by the operator 104 using suitable input peripherals and a graphic user interface (GUI) 118 which enable the operator to set parameters of the system 100. GUI 118 typically also displays results of the procedure to the operator. The software in memory 116 may be downloaded to the controller in electronic form, over a network, for example. Alternatively or additionally, the software may be provided on non-transitory tangible media such as optical, magnetic or electronic storage media.

As will be described in further detail, aspects of this disclosure involve the use of acoustic feedback to help control the delivery of RF energy during an ablation procedure or otherwise adjust the ablation. One or more acoustic sensors may be employed to detect a steam pop by transducing mechanical vibrations associated with the conversion of water from liquid to gas due to the delivery of RF energy into an electrical signal. Depending on the embodiment, the electrical signal may be amplified, processed and/or otherwise manipulated to facilitate detection of a steam pop. In one aspect, the signal from the acoustic sensor may be conveyed or indicated in any appropriate manner to operator 104, including by conversion to sound, visually (such as through GUI 118), and/or tactile indication. In response, operator 104 may adjust ablation by modulating or ceasing delivery of RF energy when the signal from the acoustic sensor indicates a steam pop has occurred. Operator 104 may also reduce the contact force of electrode 12 with the tissue being ablated. Still further, adjusting ablation may also include altering one or more aspects of the delivery of irrigation fluid, such as by increasing or decreasing the rate at which irrigation fluid is supplied, by changing the temperature of the delivered irrigation fluid or any other suitable aspect. The irrigation fluid may be supplied using a lumen in catheter 10 or may be supplied using a separate catheter. In another aspect, the acoustic sensor signal may be supplied to acoustic module 120 of system controller 112, allowing for automated identification of steam pops and/or control of ablation module 122 in any desired manner, such as by attenuating the RF energy being delivered or by discontinuing delivery. As will be appreciated, it may be desirable to activate certain aspects of the acoustic feedback system only when ablation is being performed, such as amplifying and playing the signal from the acoustic sensor or otherwise alerting operator 104.

According to this disclosure, any suitable implementation of an acoustic sensor may be employed. For example, a conventional microphone may be used as an electromechanical transducer to convert pressure waves impinging on a diaphragm into electrical impulses. As will be appreciated, other configurations of electromechanical transducers may also be employed, including but not limited to, strain gages, accelerometers, and the like, and may be used independently or in conjunction with one another. For example, the acoustic sensor may be configured as a contact microphone that responds to sound waves carried as vibrations by a medium other than air, including the skin of patient 106.

Further, a wide variety of placements and deployments of one or more acoustic sensors may be employed. In one aspect, catheter 10 may incorporate an acoustic sensor, allowing for placement within the body of patient 106 during the ablation procedure. Alternatively, or in addition, a separate diagnostic catheter 124 carrying an acoustic sensor may be disposed within patient 106. In some embodiments, this may allow the acoustic sensor to be placed at a position expected to provide improved detection of a steam pop based on the current treatment site. In another aspect, external acoustic sensor 126 may be positioned adjacent patient 106. In yet another aspect, an acoustic sensor may be incorporated into pad 128 to be applied to the skin of patient 106. As desired, pad 128 may be a single purpose device or may provide additional functionality for performing the ablation procedure, such as by incorporating a reference electrode, a counter electrode, a sensor for determining the position of catheter 10 within patient 106 or the like.

Depending upon the embodiment, any one or combination of the acoustic sensors described above, as well as other suitable examples may be used to detect a steam pop during delivery of RF energy with catheter 10. For example, any plurality of acoustic sensors may be configured as an array to allow acoustic module 120 to sound processing techniques as known in the art, including beamforming techniques to predominantly receive signals from a desired angular direction or beam steering techniques to actively direct a main lobe of the array to a desired location. In another aspect, acoustic module 120 may employ pattern matching techniques to identify an acoustic signature characteristic of a steam pop. Other suitable processing techniques, including operations in the time and/or frequency domains, may be used to facilitate identification of electrical signals from the acoustic sensor(s) that may be associated with a steam pop. For example, filtering techniques may be employed to selectively adjust the gain of specific frequency ranges, such as to amplify frequencies associated with a steam pop or to attenuate frequencies associated with background or ambient noise.

Figure 2:
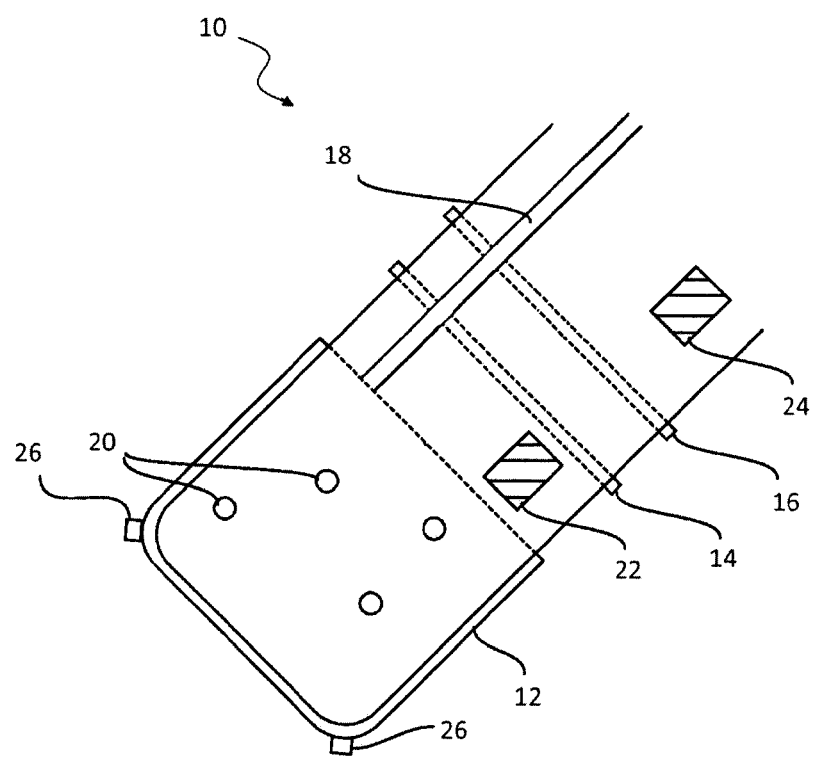
FIG. 2 is a schematic illustration of a distal portion of a catheter used in the system of FIG. 1, in accordance with an embodiment of the present invention.

Certain details regarding the distal portion of one embodiment of catheter 10 are schematically depicted in FIG. 2. Catheter 10 may include at least one electrode configured as cup electrode 12 at the distal tip of catheter 10. Additional electrodes may be configured as ring electrodes, such as electrodes 14 and 16 as shown, but any desired number of electrodes may be employed and insulated from each other. The electrodes typically comprise thin metal layers formed over an insulating substrate. Electrodes 12, 14 and 16 may be connected to system controller 112, shown in FIG. 1, such that at least one of the electrodes may be used to ablate tissue. Ablation module 122, also shown in FIG. 1, and system controller 112, may be configured to set and measure a level of the ablation power delivered by each of the electrodes. To dissipate heat resulting from the ablation procedure, irrigation fluid may be supplied through tube 18 and flow through apertures 20 of cup electrode 12. The rate of flow of irrigation fluid may be controlled by system controller 112. Further, one or more position sensors 22 may be incorporated in the distal tip to facilitate positioning and/or orienting catheter 10 within patient 106 as described above.

As described above, in some embodiments catheter 10 may incorporate acoustic sensor 24 to be disposed in patient 106 during the ablation procedure, which may be implemented using any of the noted techniques. Further, catheter 10 may also include one or more additional, non-acoustic sensors 26 (by way of example, two are shown in the diagram) which are fixedly connected, by an insulator, to the outer surface of cup electrode 12. Sensors 26 may be any combination of temperature sensors, e.g., thermistor, thermocouple, fluoroptic probe, and the like, or electrical sensors, e.g., micro-electrodes. Each sensor 26 may be potted, over molded, or otherwise encapsulated or sealed to enable contact with blood, tissue, and/or irrigation fluid. When configured as a temperature sensor, sensor 26 provides information regarding the thermal characteristics of the fluid and tissue adjacent catheter 10 during the ablation procedure. Similarly, when configured as an electrical sensor, sensor 26 provides information regarding electrical characteristics, such as impedance. Alternatively or in addition, electrodes 12, 14 and/or 16 may be used diagnostically to assess electrical characteristics in addition to delivering RF energy. In one embodiment, a counter electrode, such as pad 128, may be positioned in contact with the skin of patient 106 to complete the electrical circuit during delivery of RF energy. In other embodiments, a multipolar electrode arrangement may be provided, such as by using electrodes 12, 14 and/or 16. Electrical characteristics, such as impedance, may be measured between any of the provided electrodes.

Accordingly, signals from any number and combination of acoustic sensors, including acoustic sensor 24 in catheter 10, an acoustic sensor in diagnostic catheter 124, external acoustic sensor 126 and/or an acoustic sensor in pad 128, may be used to detect acoustic characteristics associated with a steam pop. In turn, operator 104 may control delivery of RF energy through catheter 10 in response to such signals and/or acoustic module 120 may process the signal(s) output by the acoustic sensor(s) to automatically identify a steam pop so that ablation module 122 may control delivery of RF energy in response.

As will be appreciated, the techniques of this disclosure provide a significant improvement in the threshold of detection by evaluating signals from the acoustic sensor that may be associated with a steam pop that is inaudible to operator 104. In one aspect, system 100 may be configured to amplify and play signals recorded by the acoustic sensor(s), allowing operator 104 to identify a steam pop based on personal experience. Notably, in addition to amplification, the signal may be processed as desired, such as by removing background or ambient noise using any suitable technique, by translating the frequency range to match human hearing, or the like.

In embodiments, steam pop identification and/or control of RF energy delivery may be automated using acoustic module 120 and ablation module 122. With respect to automated steam pop detection, acoustic module 120 may employ any suitable signal processing technique to identify acoustic characteristics associated with a steam pop, including without limitation assessing magnitude, frequency and/or timing characteristics. In one aspect, system 100 may be calibrated during the procedure but prior to actual ablation in order to establish baselines for background and/or ambient noise. Following identification of a steam pop, operator 104 may be alerted using a visual, auditory and/or tactile (e.g., vibration of catheter 10) warning or combination of warnings. With respect to automated control of RF energy delivery using ablation module 122 following a steam pop detection, the reaction time of the operator 104 may be avoided and the number of steam pops that may occur during a procedure can be reduced. In addition the severity of an adverse event associated with a steam pop may be reduced.

Varying degrees of automation may be provided as desired, including instant cessation of RF delivery upon identification of a steam pop. In other embodiments, the response of ablation module 122 to a steam pop identification by acoustic module 120 may be tailored. For example, instead of immediately stopping delivery of RF energy, the amount of energy may be reduced. In one aspect, the RF energy delivery may be reduced a predefined amount for each steam pop detection. In another aspect, the reduction of RF energy may be based on characteristics of the identified steam pop, such as magnitude, frequency and/or timing. As an example only and without limitation, the amount of reduction in RF energy may be correlated with the magnitude of the detected steam pop and/or the rate of irrigation may be increased accordingly or otherwise adjusted. In yet another aspect, the criteria used to identify a steam pop may be adjusted. As one example, different thresholds may be employed depending on factors such as the type of ablation procedure being performed or condition of patient 106. As another example, different identifying characteristics may be associated with different procedures or different treatment sites, such as different frequency ranges. Additionally, as described in detail below, information from the acoustic sensor(s) may be combined with information from one or more additional sensors to improve detection, such as measured temperature at the treatment site and/or impedance.

Figure 3:
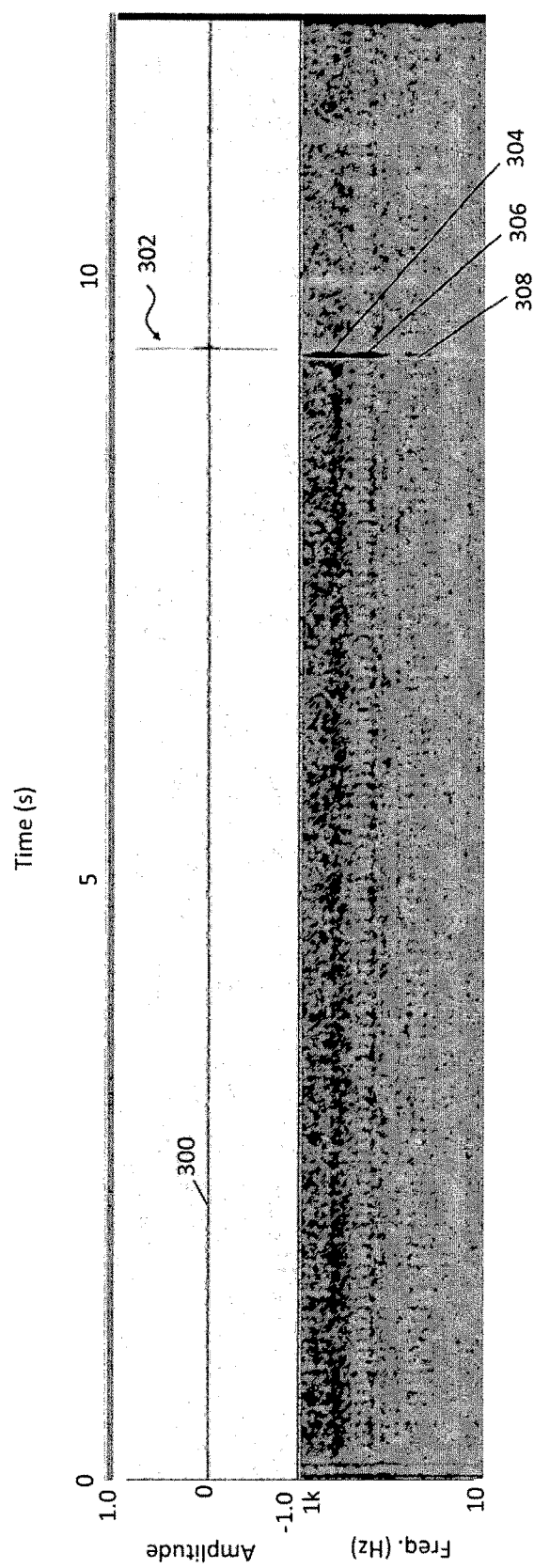
FIG. 3 is a graph illustrating a signal obtained by an acoustic sensor indicating a steam pop in accordance with an embodiment of the present invention.
Figure 4:
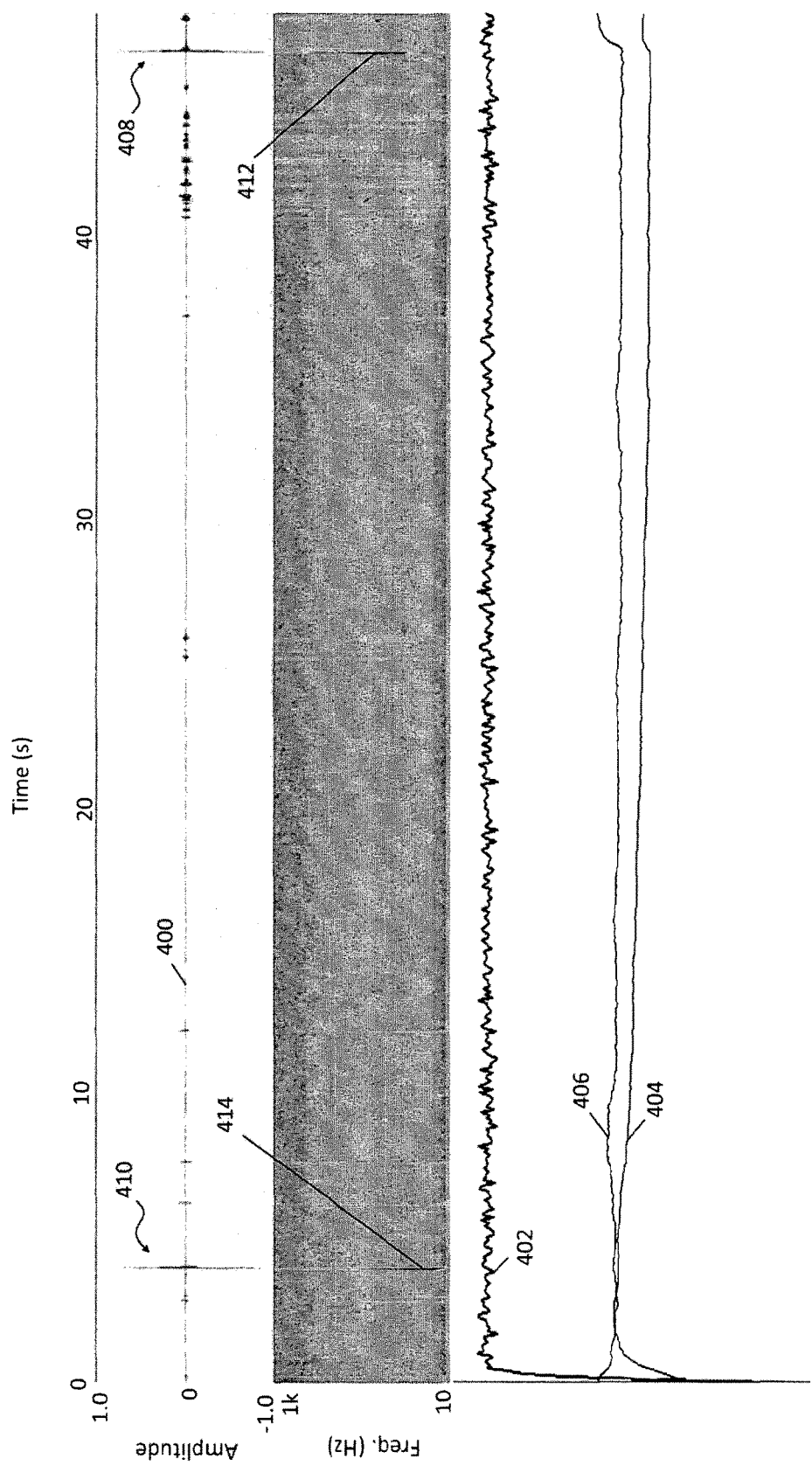
FIG. 4 is a graph illustrating a signal obtained by an acoustic sensor indicating a steam pop and information from additional sensors in accordance with an embodiment of the present invention.

To help illustrate aspects of this disclosure, examples of acoustic and other sensor signals during a steam pop are depicted in FIGS. 3 and 4. For these tests, ablation was performed on a beef heart in a saline bath at 37° C. to simulate a treatment procedure. An acoustic sensor in the form of a digital stethoscope was employed and either held in the air over the saline bath or in contact with the wall of the bath. An irrigated RF catheter was used to deliver 50W of RF energy to perform the ablation.

In the first example shown in FIG. 3, the acoustic sensor was suspended over the saline bath to mimic the performance expected from an external acoustic sensor, such as external acoustic sensor 126. Trace 300 in the upper portion of the graph depicts the amplitude of the detected signal in time domain and the lower portion depicts the corresponding spectrograph with the shading indicating the relative amplitude of the various frequency components ranging from 10 Hz to 1 kHz. Spike 302 in trace 300 occurring at approximately 9.5 s corresponds to a steam pop and may be distinguished from the baseline. When amplified, spike 302 was clearly audible to the operator during the test. Spike 302 may be characterized by an almost immediate increase to peak amplitude followed by a more drawn out return to baseline. Further, the spectrograph indicates that spike 302 includes two increased amplitude upper frequency components 304 and 306 and a lesser lower frequency component 308. Any combination of these characteristics may be used to help identify a steam pop.

Next, in the example shown in FIG. 4, the acoustic sensor was held in contact with the wall of the saline bath to provide a similar response to that expected from a contact acoustic sensor, such as may be incorporated into pad 128. Similarly to FIG. 3, trace 400 in the upper portion of the graph depicts the overall amplitude of the detected signal and the spectrograph is shown in the middle portion. Here, there lower portion of the graph shows the delivery of RF power as trace 402, along with the measured impedance as trace 404 and the temperature at the treatment site as trace 406. As shown, spike 408 in trace 400 occurring at approximately 46.5 s corresponds to a steam pop. For comparison, trace 400 also includes spike 410 occurring at approximately 4.0 s. Spike 410 resulted from background noise and did not correspond to a steam pop. Although spikes 408 and 410 exhibit similar magnitudes, distinguishing features exist. Notably, the operator was able to recognize the difference in sound when amplified. Further, spikes 408 and 410 exhibit similarly rapid increases to peak amplitude, but the return to baseline is more extended for spike 408 as compared to spike 410. Likewise, the spectrograph shows distinguishing features in the spectral components of spikes 408 and 410. For example, spike 408 exhibits an increased frequency component 412 as compared to the primary frequency component 414 of spike 410. Still further, the lower graph demonstrates that information from additional sensors may be employed to improve the confidence of steam pop detection. The impedance indicated by trace 404 has a baseline of approximately 109Ω, which exhibits an increase of approximately 4 Ω within 0.2 s that coincides with the steam pop indicated by spike 408. Similarly, the temperature indicated by trace 406 has a baseline of approximately 44° C. and increases approximately 5° C. when the steam pop occurs. In contrast, no increase in either sensor measurement is apparent when spike 410 occurs. Either or both of these characteristics may be used to validate the detection of a steam pop by the acoustic sensor(s). As desired, other characteristics measured by different sensors may also be employed.

Figure 5:
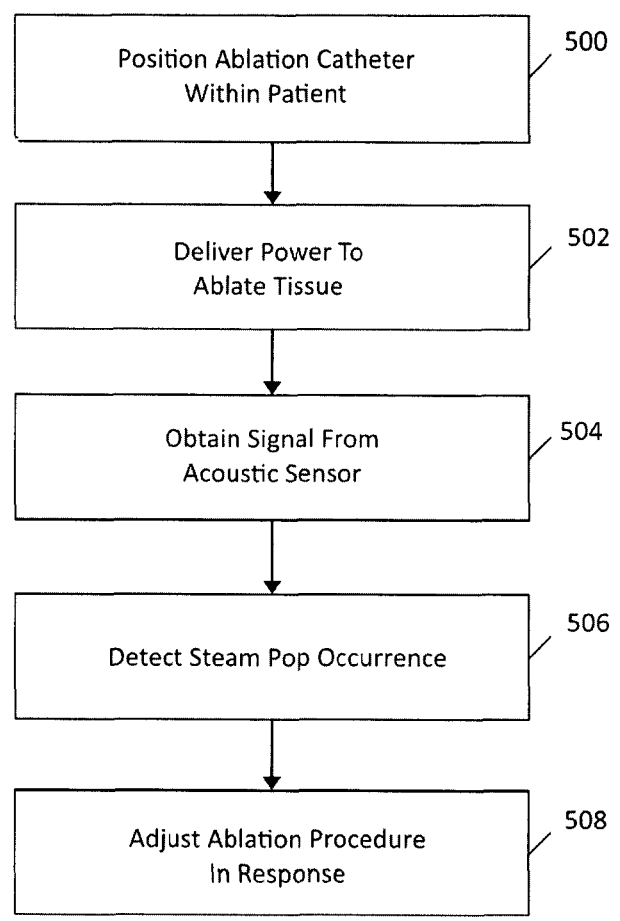
FIG. 5 is a flowchart showing a representative routine for performing an ablation procedure in accordance with an embodiment of the present invention.

According to the discussion above, a suitable routine for performing an ablation procedure may be represented by the flowchart shown in FIG. 5. Beginning with 500, an ablation catheter, such as catheter 10, may be inserted in patient 106 so that at least electrode 12 is positioned adjacent a desired treatment site. In 502, power is delivered to at least electrode 12 to ablate tissue at the treatment site. Next, in 504, a signal may be obtained from an acoustic sensor for use in detecting occurrence of a steam pop. The acoustic sensor may be any one or combination of acoustic sensor 24 carried by catheter 10, the acoustic sensor of diagnostic catheter 124, external acoustic sensor 126, an acoustic sensor incorporated into pad 128, or others. A steam pop occurrence may be detected in 506 using the signal from the acoustic sensor. In turn, the ablation procedure may be adjusted in 508 as a result of the detection.

Described herein are certain exemplary embodiments. However, one skilled in the art that pertains to the present embodiments will understand that the principles of this disclosure can be extended easily with appropriate modifications to other applications.

What is claimed is:

1. A method for the ablation of a portion of tissue of a patient by an operator comprising:
    inserting an ablation catheter having an electrode into the patient;
    connecting the catheter to a system controller capable of delivering power to the electrode, the system controller comprising an acoustic module configured to receive an acoustic sensor signal and information from a first additional sensor, the information comprises a change in impedance measured by the first additional sensor;
    delivering power to the electrode to ablate tissue;
    obtaining a signal from the acoustic sensor;
    obtaining the information from the first additional sensor;
    detecting occurrence of a steam pop based at least in part on the acoustic sensor signal;
    identifying a steam pop with the acoustic module based at least in part on the acoustic sensor signal;
    validating the identification of the steam pop based on the change in impedance received from the first additional sensor; and
    automatically adjusting the ablation in response to measured characteristics of the identified and validated steam pop.

2. The method of claim 1, wherein adjusting the ablation comprises one of ceasing delivery of power to the electrode, attenuating the power delivered to the electrode, reducing a contact force of the electrode and altering delivery of irrigation fluid.

3. The method of claim 2, wherein attenuating the power is based at least in part on a characteristic determined from the acoustic sensor signal.

4. The method of claim 1, wherein obtaining the signal from the acoustic sensor comprises one of positioning the acoustic sensor adjacent the patient, positioning the acoustic sensor in contact with the patient, positioning the acoustic sensor within the patient and deploying a plurality of acoustic sensors.

5. The method of claim 4, wherein the acoustic sensor is carried by the ablation catheter.

6. The method of claim 1, wherein obtaining the signal from the acoustic sensor further comprises processing the signal to facilitate identification of a steam pop.

7. The method of claim 1, wherein the steam pop is further identified based at least in part on a change in temperature measured by a second additional sensor.

8. The method of claim 1, further comprising alerting the operator when the acoustic module identifies a steam pop.

9. The method of claim 1, further comprising adjusting an identification criterion employed by the acoustic module.

10. The method of claim 1, wherein automatically adjusting the ablation comprises automatically adjusting the delivery of power to the electrode when the acoustic module identifies a steam pop.

11. The method of claim 1, wherein automatically adjusting the ablation comprises automatically ceasing delivery of power to the electrode when the acoustic module identifies a steam pop.

12. The method of claim 1, further comprising automatically adjusting delivery of irrigation fluid when the acoustic module identifies a steam pop.

13. The method of claim 1, wherein the measured characteristics of the identified steam pop comprises magnitude of the steam pop.

14. The method of claim 1, wherein the measured characteristics of the identified steam pop comprises frequency of the steam pop.

15. The method of claim 1, wherein the measured characteristics of the identified steam pop comprises timing of the steam pop.

16. A catheter comprising:
    an elongated body;
    an electrode mounted at a distal end of the elongated body, wherein the electrode is configured to deliver energy to ablate tissue;
    an acoustic sensor configured to output a signal that may be used to detect an occurrence of a steam pop;
    a first additional sensor configured to output a change in impedance signal, wherein the electrode is configured to automatically adjust the ablation in response to measured characteristics of an identified steam pop, wherein the steam pop is identified based at least in part on the acoustic sensor signal and validated based on the change in impedance received from the first additional sensor.

17. The catheter of claim 16, further comprising a temperature sensor mounted at the distal end of the elongated body.

18. An ablation system comprising:
an ablation catheter having an electrode configured to be inserted into a patient;
a system controller capable of delivering power to the electrode;
an acoustic sensor configured to output a signal that may be used to detect an occurrence of a steam pop;
a first additional sensor configured to output a change in impedance signal that is capable of being used to detect an occurrence of the steam pop;
an acoustic module configured to identify a steam pop based at least in part on the acoustic sensor signal and further configured to validate the steam pop based on the change in impedance signal; and
an ablation module configured to automatically adjust the delivery of power to the electrode when the acoustic module identifies a steam pop, the adjustment based on characteristics of the identified steam pop.

19. The system of claim 18, further comprising an ablation module configured to alter delivery of irrigation fluid.

20. The system of claim 18, further comprising a second additional sensor, wherein the acoustic module is further configured to receive information from the second additional sensor and to identify the steam pop based at least in part on the information from the additional sensor.

21. The system of claim 20, wherein the second additional sensor measures temperature.

22. The system of claim 18, further comprising an indicator configured to alert an operator when the acoustic module identifies a steam pop.

23. The system of claim 18, further comprising an ablation module configured to automatically alter delivery of irrigation fluid when the acoustic module identifies a steam pop.

* * * * *